(12) United States Patent
Yang et al.

(10) Patent No.: US 11,232,560 B2
(45) Date of Patent: Jan. 25, 2022

(54) METHOD AND APPARATUS FOR PROCESSING FUNDUS IMAGE

(71) Applicant: Beijing Baidu Netcom Science And Technology Co., LTD., Beijing (CN)

(72) Inventors: Yehui Yang, Beijing (CN); Yanwu Xu, Beijing (CN); Lei Wang, Beijing (CN); Yan Huang, Beijing (CN)

(73) Assignee: Beijing Baidu Netcom Science and Technology Co., Ltd.

( * ) Notice: Subject to any disclaimer, the term of this patent is extended or adjusted under 35 U.S.C. 154(b) by 103 days.

(21) Appl. No.: 16/701,025

(22) Filed: Dec. 2, 2019

(65) Prior Publication Data

US 2020/0320686 A1 Oct. 8, 2020

(30) Foreign Application Priority Data

Apr. 4, 2019 (CN) .......................... 201910269661.7

(51) Int. Cl.
*G06T 7/00* (2017.01)
*G06T 7/11* (2017.01)
(Continued)

(52) U.S. Cl.
CPC .......... *G06T 7/0012* (2013.01); *A61B 3/0025* (2013.01); *A61B 3/12* (2013.01);
(Continued)

(58) Field of Classification Search
CPC ......... G06T 7/0012; G06T 7/11; G06T 7/174; G06T 2207/20021; G06T 2207/20081;
(Continued)

(56) References Cited

U.S. PATENT DOCUMENTS

| 2007/0002275 | A1* | 1/2007 | Yan ....................... G06T 7/0012 351/200 |
| 2015/0110372 | A1* | 4/2015 | Solanki ................. G16H 30/20 382/130 |
| 2018/0315193 | A1* | 11/2018 | Paschalakis ............. G06N 3/08 |
| 2020/0085290 | A1* | 3/2020 | Wang .................... G06T 7/0014 |
| 2020/0160521 | A1* | 5/2020 | Wang ................... A61B 3/0025 |

FOREIGN PATENT DOCUMENTS

| CN | 106408564 A | 2/2017 |
| CN | 108038843 A | 5/2018 |

(Continued)

OTHER PUBLICATIONS

María García, María I. López, Daniel Álvarez, Roberto Hornero, "Assessment of four neural network based classifiers to automatically detect red lesions in retinal images," Medical Engineering & Physics, vol. 32, Issue 10, 2010, pp. 1085-1093, (Year: 2010).*

(Continued)

*Primary Examiner* — Utpal D Shah
(74) *Attorney, Agent, or Firm* — Weaver Austin Villeneuve & Sampson LLP

(57) ABSTRACT

Embodiments of the present disclosure provide a method and apparatus for processing a fundus image. The method may include: acquiring a target fundus image; dividing the target fundus image into at least two first image blocks; inputting a first image block into a pre-trained deep learning model, to obtain a first output value; and determining, based on the first output value and a threshold, whether the first image block is the fundus image block containing a predetermined type of image region.

20 Claims, 6 Drawing Sheets

(51) Int. Cl.
*G06T 7/174* (2017.01)
*G06N 20/00* (2019.01)
*A61B 3/00* (2006.01)
*A61B 3/12* (2006.01)
*G06K 9/62* (2006.01)

(52) U.S. Cl.
CPC .......... *G06K 9/6256* (2013.01); *G06N 20/00* (2019.01); *G06T 7/11* (2017.01); *G06T 7/174* (2017.01); *G06T 2207/20021* (2013.01); *G06T 2207/20081* (2013.01); *G06T 2207/30041* (2013.01)

(58) Field of Classification Search
CPC .......... G06T 2207/30041; G06N 20/00; A61B 3/0025; A61B 3/12; G06K 9/6256
See application file for complete search history.

(56) References Cited

FOREIGN PATENT DOCUMENTS

| | | | |
|---|---|---|---|
| CN | 108231194 | A | 6/2018 |
| CN | 108629378 | A | 10/2018 |
| CN | 108921206 | A | 11/2018 |
| CN | 109102889 | A | 12/2018 |
| CN | 109410179 | A | 3/2019 |

OTHER PUBLICATIONS

Akcay, S. et al., "GANomaly Semi-Supervised Anomaly Detection via Adversarial Training," Department of {Computer Science1, Engineering2}, Durham University, UK, arXiv:1805.06725v3 [cs.CV] Nov. 13, 2018, 16 pages.

* cited by examiner

METHOD AND APPARATUS FOR PROCESSING FUNDUS IMAGE

CROSS-REFERENCE TO RELATED APPLICATIONS

This application claims priority to Chinese Patent Application No. 201910269661.7, filed with the China National Intellectual Property Administration (CNIPA) on Apr. 4, 2019, the contents of which are incorporated herein by reference in their entirety.

TECHNICAL FIELD

Embodiments of the present disclosure relate to the field of computer technology, and specifically to a method and apparatus for processing a fundus image.

BACKGROUND

With the development of science and technology, the computer image processing technology has been gradually applied to more and more fields. Currently, for the processing of a fundus image, a general image processing method is desired.

The fundus is the tissue in the back, interior part of the eyeball. The fundus is the intima of the eyeball, and includes a retina, an optic papilla, a macula, and central retinal arteries and veins.

SUMMARY

Embodiments of the present disclosure provide a method and apparatus for processing a fundus image.

According to a first aspect, some embodiments of the present disclosure provide a method for processing a fundus image, the method includes: acquiring a target fundus image; dividing the target fundus image into at least two first image blocks; inputting a first image block into a pre-trained deep learning model, to obtain a first output value, wherein the deep learning model is used to characterize a corresponding relationship between an image block and an output value; and determining, based on the first output value and a threshold, whether the first image block is a fundus image block containing a predetermined type of image region, wherein the threshold is determined by the following steps: acquiring a fundus image containing the predetermined type of image region, and determining the threshold based on the fundus image containing the predetermined type of image region and the deep learning model.

In some embodiments, the method further includes: adding, in response to determining that the first image block is the fundus image block containing the predetermined type of image region, a label to the first image block, and outputting the first image block with the label.

In some embodiments, the determining, based on the first output value and a threshold, whether the first image block is a fundus image block containing a predetermined type of image region includes: determining whether the first output value is greater than the threshold; determining, in response to the first output value being greater than the threshold, the first image block as the fundus image block containing the predetermined type of image region; and determining, in response to the first output value being smaller than or equal to the threshold, the first image block as a fundus image block not containing the predetermined type of image region.

In some embodiments, the threshold is determined through: acquiring fundus images containing the predetermined type of image region; inputting the fundus images containing the predetermined type of image region into the deep learning model, to obtain second output values; and determining the threshold from the second output values.

In some embodiments, the threshold is determined through: acquiring a fundus image containing the predetermined type of image region; dividing the fundus image containing the predetermined type of image region into at least two second image blocks; inputting the at least two second image blocks into the deep learning model respectively to obtain at least two third output values; and selecting a maximum value from the at least two third output values as the threshold.

In some embodiments, the deep learning model is obtained through: acquiring a first training sample set, wherein a first training sample includes a fundus image not containing the predetermined type of image region and a preset value matching the fundus image not containing the predetermined type of image region; and training using fundus images not containing the predetermined type of image region of the first training samples in the first training sample set as inputs, and using preset values matching the input fundus images not containing the predetermined type of image region as desired outputs, to obtain the deep learning model.

In some embodiments, the deep learning model is obtained by training through: acquiring a second training sample set, wherein a second training sample includes at least two third image blocks not containing the predetermined type of image region and preset values matching the third image blocks, and the at least two third image blocks not containing the predetermined type of image region are obtained by dividing the fundus image not containing the predetermined type of image region; and training using the third image blocks of the second training samples in the training sample set as inputs, and using the preset values matching the third image blocks as desired outputs, to obtain the deep learning model.

According to a second aspect, some embodiments of the present disclosure provide an apparatus for processing a fundus image, the apparatus includes: a target fundus image acquiring unit, configured to acquire a target fundus image; a first image block dividing unit, configured to divide the target fundus image into at least two first image blocks; a first output value acquiring unit, configured to input a first image block into a pre-trained deep learning model, to obtain a first output value, wherein the deep learning model is used to characterize a corresponding relationship between an image block and an output value; and a first processing unit, configured to determine, based on the first output value and a threshold, whether the first image block is a fundus image block containing a predetermined type of image region, wherein the threshold is determined by the following steps: acquiring a fundus image containing the predetermined type of image region, and determining the threshold based on the fundus image containing the predetermined type of image region and the deep learning model.

In some embodiments, the apparatus further includes: an output unit, configured to add, in response to determining that the first image block is the fundus image block containing the predetermined type of image region, a label to the first image block, and output the first image block with the label.

In some embodiments, the first processing unit includes: a comparing module, configured to determine whether the first output value is greater than the threshold; a first determining module, configured to determine, in response to the first output value being greater than the threshold, the first image block as the fundus image block containing the predetermined type of image region; and a second determining module, configured to determine, in response to the first output value being smaller than or equal to the threshold, the first image block as a fundus image block not containing the predetermined type of image region.

In some embodiments, the threshold is determined by: a first acquiring unit, configured to acquire fundus images containing the predetermined type of image region; a second output value acquiring unit, configured to input the fundus images containing the predetermined type of image region into the deep learning model, to obtain second output values; and a first threshold determining unit, configured to determine the threshold from the second output values.

In some embodiments, the threshold is determined by: a second acquiring unit, configured to acquire a fundus image containing the predetermined type of image region; a second image block dividing unit, configured to divide the fundus image containing the predetermined type of image region into at least two second image blocks; a third output value acquiring unit, configured to input the at least two second image blocks into the deep learning model respectively to obtain at least two third output values; and a second threshold determining unit, configured to select a maximum value from the at least two third output values as the threshold.

In some embodiments, the deep learning model is obtained by training through following units: a first training sample set acquiring unit, configured to acquire a first training sample set, wherein a first training sample includes a fundus image not containing the predetermined type of image region and a preset value matching the fundus image not containing the predetermined type of image region; and a first training unit, configured to train using fundus images not containing the predetermined type of image region of the first training samples in the first training sample set as inputs, and using preset values matching the input fundus images not containing the predetermined type of image region as desired outputs, to obtain the deep learning model.

In some embodiments, the deep learning model is obtained by training through following units: a second training sample set acquiring unit, configured to acquire a second training sample set, wherein a second training sample includes at least two third image blocks not containing the predetermined type of image region and preset values matching the third image blocks, and the at least two third image blocks not containing the predetermined type of image region are obtained by dividing the fundus image not containing the predetermined type of image region; and a second training unit, configured to train using the third image blocks of the second training samples in the training sample set as inputs, and using the preset values matching the third image blocks as desired outputs, to obtain the deep learning model.

According to a third aspect, some embodiments of the present disclosure provide an electronic device, the electronic device includes: one or more processors; and a storage apparatus, storing one or more programs; where the one or more programs, when executed by the one or more processors, cause the one or more processors to implement the method according to any one of the implementations of the first aspect.

According to a fourth aspect, some embodiments of the present disclosure provide a computer-readable medium, storing a computer program thereon, where the computer program, when executed by a processor, causes the processor to implement the method according to any one of the implementations of the first aspect.

The method and apparatus for processing a fundus image provided by some embodiments of the present disclosure, acquires a target fundus image; divides the target fundus image into at least two first image blocks; inputs a first image block into a pre-trained deep learning model, to obtain a first output value, wherein the deep learning model is used to characterize a corresponding relationship between an image block and an output value; and then determines, based on the first output value and a threshold, whether the first image block is a fundus image block containing a predetermined type of image region, where the threshold is determined by the following steps: acquiring a fundus image containing the predetermined type of image region, and determining the threshold based on the fundus image containing the predetermined type of image region and the deep learning model. In the embodiments of the present disclosure, since the deep learning model is obtained through pre-training, the target image is divided into first image blocks and a first image block is input into the pre-trained deep learning model to obtain a first output value, and then whether the first image block is a block including a predetermined type of image region is determined based on the first output value and the threshold. Therefore, the processing speed of a processor on the target fundus image can be improved, and the amount of calculation of the processor can be reduced.

BRIEF DESCRIPTION OF THE DRAWINGS

After reading detailed descriptions of non-limiting embodiments with reference to the following accompanying drawings, other features, objectives and advantages of the present disclosure will become more apparent.

DETAILED DESCRIPTION OF EMBODIMENTS

Embodiments of present disclosure will be described below in detail with reference to the accompanying drawings. It should be appreciated that the specific embodiments described herein are merely used for explaining the relevant disclosure, rather than limiting the disclosure. In addition, it should be noted that, for the ease of description, only the parts related to the relevant disclosure are shown in the accompanying drawings.

It should also be noted that the some embodiments in the present disclosure and some features in the disclosure may be combined with each other on a non-conflict basis. Features of the present disclosure will be described below in detail with reference to the accompanying drawings and in combination with embodiments.

Figure 1:
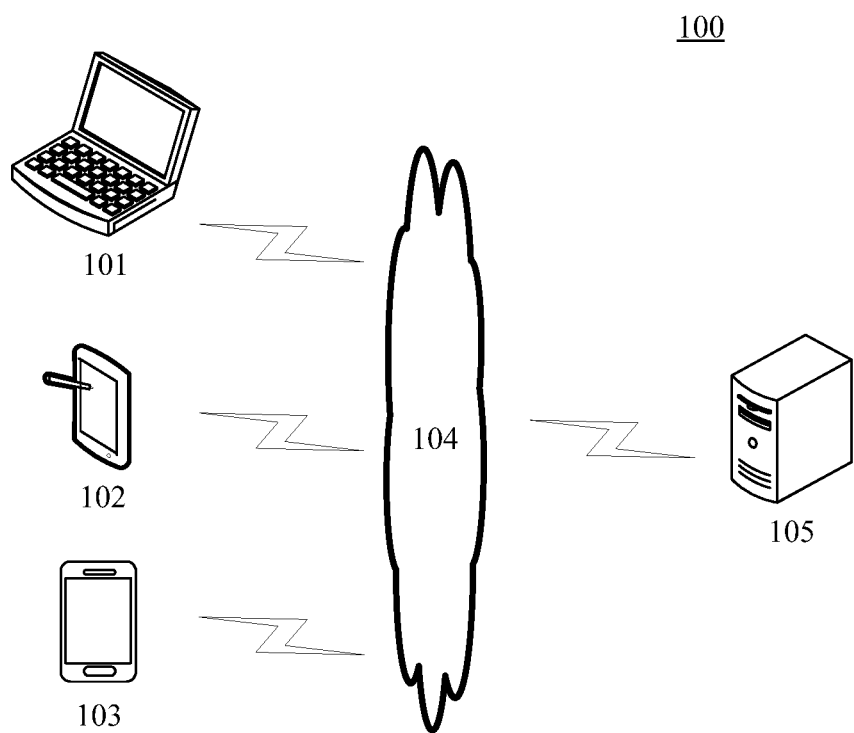
FIG. 1 is an architectural diagram of an example system to which an embodiment of the present disclosure may be applied.

FIG. 1 shows an example architecture 100 to which a method for processing a fundus image or an apparatus for processing a fundus image may be applied.

As shown in FIG. 1, the system architecture 100 may include a terminal device 101, 102 or 103, a network 104, and a server 105. The network 104 serves as a medium providing a communication link between the terminal device 101, 102 or 103 and the server 105. The network 104 may include various types of connections, such as wired or wireless communication links, or optical fiber cables.

The terminal device 101, 102 or 103 may interact with the server 105 through the network 104 to receive or send messages, etc. The terminal device 101, 102 or 103 may be installed with various communication client applications, such as web browser applications, image processing applications, search applications, instant messaging tools, e-mail clients, social platform software, text editing applications, and reading applications.

The terminal device 101, 102 or 103 may be hardware or software. When the terminal device 101, 102 or 103 is hardware, the terminal device may be various types of electronic devices with display screens and supporting communication with the server, including but not limited to a smart phone, a tablet computer, an e-book reader, an MP3 (Moving Picture Experts Group Audio Layer III) player, an MP4 (Moving Picture Experts Group Audio Layer IV) player, a laptop computer, a desktop computer, etc. When the terminal device 101, 102 or 103 is software, the terminal device may be installed in the above-listed electronic devices. The terminal device may be implemented as a plurality of software programs or software modules (e.g., for providing distributed services), or as a single software program or software module. Specific limitations are not provided herein.

The server 105 may be a server providing various services, for example, a backend server for analyzing a fundus image output by the terminal device 101, 102 or 103. The backend server may process a target fundus image and generate a processing result.

It should be noted that the server may be hardware or software. When the server is hardware, the server may be implemented as a distributed server cluster composed of multiple servers, or implemented as a single server. When the server is software, the server may be implemented as a plurality of software programs or software modules (e.g., for providing distributed services), or as a single software program or software module. Specific limitations are not provided herein.

It should be noted that the method for processing a fundus image according to some embodiments of the present disclosure may be performed by the server 105. Accordingly, the apparatus for processing a fundus image may be provided in the server 105.

It should be understood that the numbers of the terminal devices, the network and the server in FIG. 1 are merely illustrative. Any number of terminal devices, networks and servers may be provided based on actual requirements.

Figure 2:
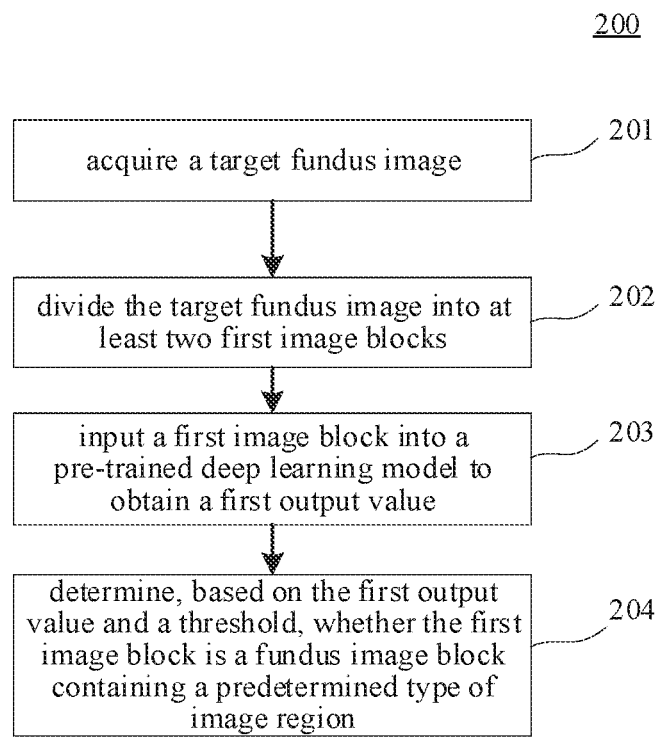
FIG. 2 is a flowchart of a method for processing a fundus image according to an embodiment of the present disclosure.

Further referring to FIG. 2, a flow 200 of a method for processing a fundus image according to an embodiment of the present disclosure is shown. The method for processing a fundus image, applied to a server, includes the following steps.

Step 201: acquiring a target fundus image.

In the present embodiment, the target fundus image usually refers to a fundus image needs to be processed. As an example, the target fundus image may be from a third party device, or may be taken from an autopsy image.

In the present embodiment, the executing body (for example, the server 105 shown in FIG. 1) of the method for processing a fundus image may acquire the target fundus image. Specifically, the executing body may acquire the target fundus image pre-stored locally, or acquire the target fundus image sent by an electronic device (for example, the terminal device shown in FIG. 1) in communication connection thereto.

Step 202: dividing the target fundus image into at least two first image blocks.

In the present embodiment, the executing body may divide, after acquiring the target fundus image, the target fundus image into at least two first image blocks. As an example, the executing body may divide the target fundus image according to a preset division rule (for example, dividing one image into 64×64 image blocks that are not overlapped). As another example, the executing body may randomly divide the target fundus image. The number of the first image blocks finally obtained is not less than 2.

Step 203: inputting a first image block into a pre-trained deep learning model to obtain a first output value.

In the present embodiment, after dividing the target fundus image into at least two first image blocks, the executing body may input a first image blocks into the pre-trained deep learning model to obtain a first output value. That is, each first image block may be respectively input into the deep learning model to obtain a first output value matching each first image block. The deep learning model may be used to characterize a corresponding relationship between an image block and an output value. It should be noted that the deep learning model may be pre-trained by the executing body, or by other third party device, which is not limited by the present embodiment.

In the present embodiment, the deep learning model may be pre-trained by the executing body. The server may train the deep learning model capable of characterizing the corresponding relationships between image blocks and output values in a variety of ways. As an example, the server may generate a corresponding relationship table storing a plurality of corresponding relationships between image blocks and output values based on statistics on a large number of image blocks and output values, and use the corresponding relationship table as the deep learning model. In this way, the server may sequentially compare a first image block with the plurality of image blocks in the corresponding relationship table, and if an image block in the corresponding relationship table is same as or similar to the first image block, use the output value corresponding to the image block in the corresponding relationship table as a first output value corresponding to the first image block.

As another example, in some alternative implementations of the present embodiment, the deep learning model is trained by the executing body through the following steps.

Step 1: acquiring a first training sample set.

In the alternative implementation, a first training sample includes a fundus image that does not contain the predetermined type of image region and a preset value matching the fundus image that does not contain the predetermined type of image region.

In the alternative implementation, the executing body may acquire the first training sample set. For example, the executive body acquires a plurality of fundus images that do not contain the predetermined type of image region. The preset value matching the fundus image that does not contain the predetermined type of image region is, for example, "0".

Step 2: training using fundus images of first training samples in the first training sample set that do not contain the predetermined type of image region as inputs, and using preset values matching the input fundus images that do not contain the predetermined type of image region as desired outputs, to obtain the deep learning model.

In the alternative implementation, the executing body may train an initialized deep learning model. The initialized deep learning model may be a deep learning model that is not trained or not completely trained. Each layer of the initialized deep learning model may be set with initial parameters. These parameters may be continually adjusted during the training of the deep learning model.

Specifically, the executing body may first use the fundus images of the first training samples that do not contain the predetermined type of image region in the first training sample set as inputs, use the preset values matching the input fundus images that do not contain the predetermined type of image region as desired outputs, and calculate differences between actual output values and the preset values by using a preset loss function. Then, the parameters of the initialized deep learning model may be adjusted based on the calculated differences, and the training ends if a preset training ending condition is satisfied. For example, the preset training ending condition here may include, but is not limited to, at least one of the following: the training time exceeds a preset time length, the training times exceeds a preset number, and calculated differences are smaller than a preset difference threshold.

In this way, the executing body may input a target fundus image block or a target fundus image into the deep learning model from an input side, the target fundus image block or the target fundus image is sequentially processed by the parameters of each layer in the deep learning model, and output from an output side of the deep learning model, and the information output from the output side is the output value matching the target fundus image block or the target fundus image.

As a further example, in some alternative implementations of the present embodiment, the deep learning model is trained by the executing body through the following steps.

Step 1: acquiring a second training sample set.

In the alternative implementation, a second training sample includes at least two third image blocks that do not contain the predetermined type of image region and preset values matching the third image blocks. The at least two third image blocks that do not contain the predetermined type of image region are obtained by dividing the fundus image that does not contain the predetermined type of image region by the executing body.

In the alternative implementation, the executing body may acquire the second training sample set. For example, the executing body acquires a plurality of third image blocks that do not contain a predetermined type of image region. The preset values matching the third image blocks are, for example, "0".

Step 2: training using third image blocks of second training samples in the training sample set as inputs, and using preset values matching the third image blocks as desired outputs, to obtain the deep learning model.

In the alternative implementation, the executing body may divide the fundus image that does not contain the predetermined type of image region into a plurality of third image blocks. Then, the preset values matching the third image blocks may be set to "0". As an example, the executing body may use the third image blocks as inputs, use 0 as desired outputs, and use MSE (mean-square error) as a loss function, the training formula is:

$$\min_f L(f) = \sum_x \|f(x) - 0\|^2$$

x represents a third image block; f(x) represents a deep learning model; 0 represents a desired output; f represents f(x), and may be interpreted as a variable; L(f) represents a loss function.

The specific process of adjusting the parameters of the initialized deep learning model is same as that described in the above implementation, and details are not described herein again. Thus, the deep learning model f(x) is obtained by training.

Step 204: determining, based on the first output value and a threshold, whether the first image block is a fundus image block containing a predetermined type of image region.

In the present embodiment, after obtaining the first output value, the executing body may determine, based on the first output value and the threshold, whether the first image block is the fundus image block containing the predetermined type of image region. In the present embodiment, the threshold may be determined by the following steps.

Step 1: acquiring fundus images containing the predetermined type of image region.

The fundus image containing the predetermined type of image region (for example, a fundus image with a lesion image region), the fundus images containing such region may be from a third party device or from autopsy.

Step 2: determining the threshold based on the fundus images containing the predetermined type of image region and the deep learning model.

As an example, in some alternative implementations of the present embodiment, after acquiring a fundus image containing the predetermined type of image region, the executing body may input the fundus image containing the predetermined type of image region into the trained deep learning model. It can be seen from the above description that the deep learning model can output an actual output value. The actual output value here is a second output value. Since there is usually a plurality of fundus images containing the predetermined type of image region, a plurality of second output values are also obtained. Then, a maximum value is selected from these second output values as the threshold.

As another example, in some alternative implementations of the present embodiment, the executing body may divide, after acquiring a fundus image containing the predetermined type of image region, the fundus image containing the predetermined type of image region into at least two second image blocks. Then, the at least two second image blocks are respectively input into the deep learning model. It can be seen from the above description that, after each second image block is input into the deep learning model, the deep learning model can output an actual output value. The actual output value here is a third output value. Since there is usually a plurality of second image blocks, a plurality of third output values are also obtained. Then, a maximum value is selected from these third output values as the threshold.

In the present embodiment, the executing body may determine, based on the first output value and the threshold, whether the first image block is a fundus image block containing the predetermined type of image region.

As an example, the executing body may store a list of corresponding relationships between the differences between the output values and the threshold and first indication information (e.g., "1") characterizing the fundus image blocks containing the predetermined type of image region. The corresponding relationship list may also store corresponding relationships between the output values and the threshold and second indication information (e.g., "1") characterizing the fundus image blocks not containing the predetermined type of image region. In this way, after obtaining a first output value, the server may first find the difference between the first output value and the threshold. Then, the indication information matching the difference is queried from the corresponding relationship list. If the indication information matching the difference is the first indication information (for example, "1" indicates that the first image block has a lesion image), it is characterized that the first image block contains the predetermined type of image region. If the indication information matching the difference is the second indication information (for example, "0" indicates that the first image block does not have a lesion image), it is characterized that the first image block does not contain the predetermined type of image region.

As another example, optionally, after obtaining a first output value, the executing body may determine whether the first output value is greater than the threshold. In response to the first output value being greater than the threshold, the executing body may determine the first image block as a fundus image block that contains the predetermined type of image region. In response to the first output value being smaller than or equal to the threshold, the executing body may determine the first image block as a fundus image block that does not contain the predetermined type of image region.

Figure 3:
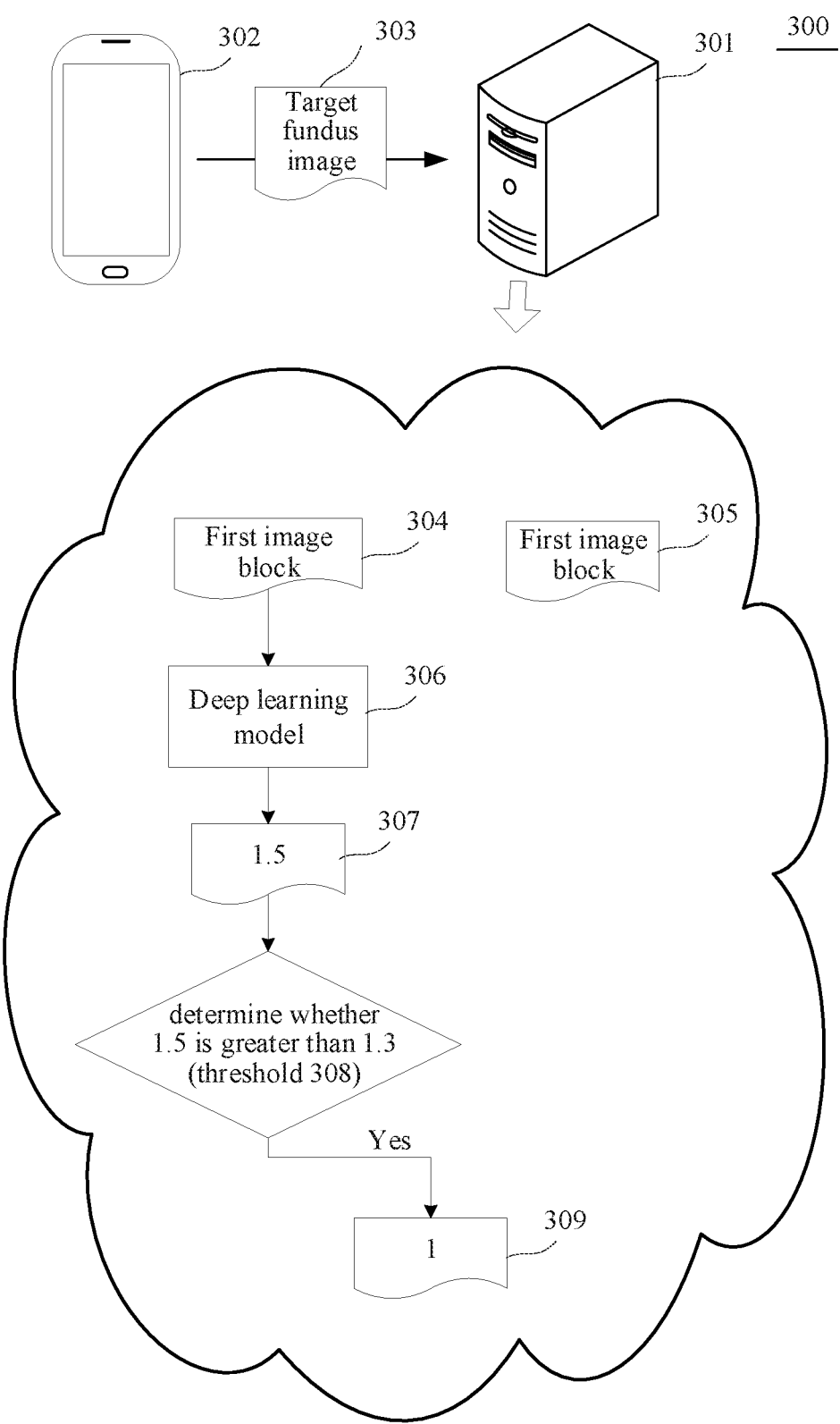
FIG. 3 is a schematic diagram of an application scenario of the method for processing a fundus image according to an embodiment of the present disclosure.

Further refer to FIG. 3, which is a schematic diagram of an application scenario of the method for processing a fundus image according to some embodiments of the present disclosure. In the application scenario of FIG. 3, a server 301 acquires a target fundus image 303 sent from a mobile phone 302. Then, the server 301 divides the target fundus image into the first image block 304 and the first image block 305. Thereafter, the first image block 304 is input to a pre-trained deep learning model 306. The deep learning model outputs 1.5 (a first output value 307). The server 301 then compares the value 1.5 with 1.3 (a threshold 308). That is, the server 301 determines whether the 1.5 is greater than 1.3? The server determines that the 1.5 is greater than 1.3, and therefore, the server 301 determines that the first image block is a fundus image block containing a white spot, and outputs information "1" (first indication information 309). The above process may also be performed on the first image block 305, and details are not described herein again.

At present, one of the existing technologies usually relies on an image segmentation algorithm to perform pixel-level annotation on training data. This process requires a lot of time and effort. Moreover, the training of an image segmentation network is complicated and consumes a large amount of computing resources. However, according to the method provided by the above embodiments, a target fundus image is acquired and divided into at least two first image blocks; a first image block is then input to a pre-trained deep learning model to obtain a first output value. Since the deep learning model is obtained through pre-training, the processing speed of a processor on the target fundus image can be improved, and the amount of calculation of the processor can be reduced. Moreover, whether the first image block is a fundus image block containing a predetermined type of image region is determined based on the first output value and the threshold, which can also reduce the amount of calculation of the processor and reduce the time for processing the fundus image.

Figure 4:
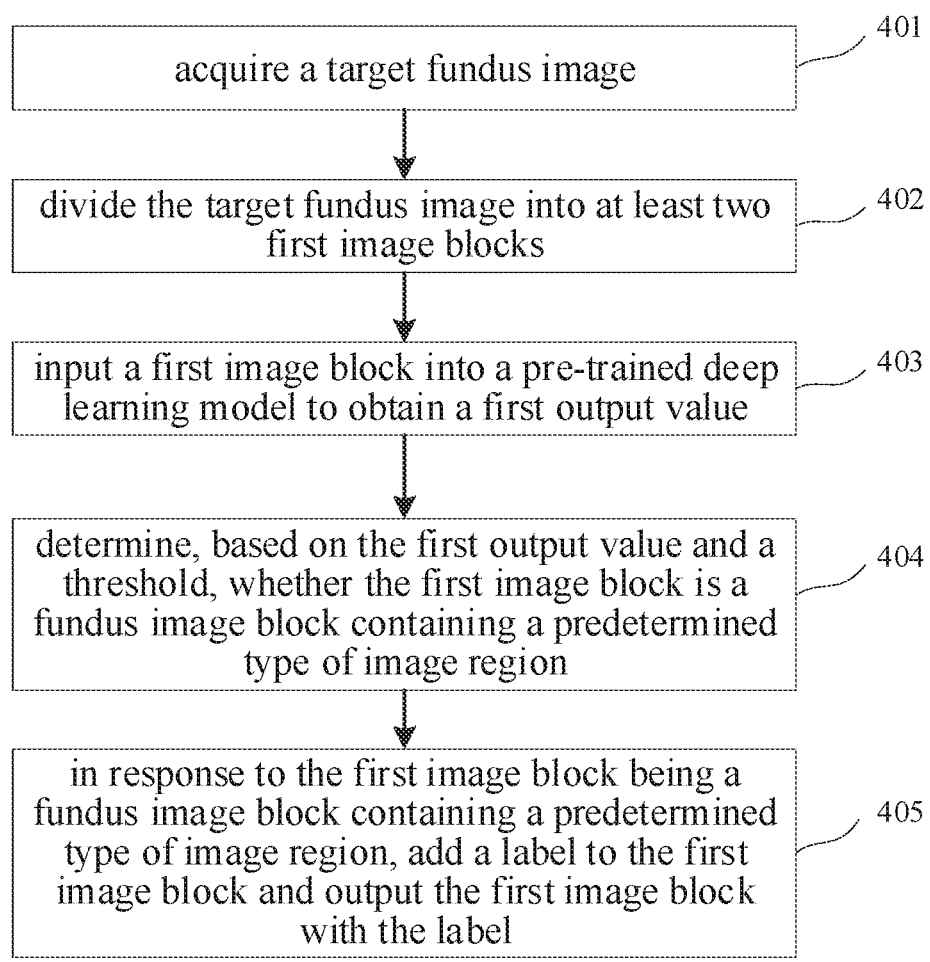
FIG. 4 is a flowchart of the method for processing a fundus image according to another embodiment of the present disclosure.

Further referring to FIG. 4, a flow 400 of the method for processing a fundus image according to another embodiment is shown. The method for processing a fundus image, applied to a server, includes the following steps.

Step 401: acquiring a target fundus image.

Step 402: dividing the target fundus image into at least two first image blocks.

Step 403: inputting a first image block into a pre-trained deep learning model to obtain a first output value.

Step 404: determining, based on the first output value and a threshold, whether the first image block is a fundus image block containing a predetermined type of image region.

In the present embodiment, steps 401, 402, 403, and 404 are respectively consistent with steps 201, 202, 203, and 204 in the foregoing embodiment, the descriptions of steps 201, 202, 203, and 204 also apply to steps 401, 402, 403, and 404, and details are not described herein again.

Step 405: adding, in response to determining that the first image block is fundus image block containing the predetermined type of image region, a label to the first image block, and outputting the first image block with the label.

In the present embodiment, in response to determining that the first image block is a fundus image block containing a predetermined type of image region, the executing body may further add a label to the first image block. The first image block with the label is then output. The label here may be represented by numbers or letters. For example, the fundus image block containing the predetermined type of image region may be represented by the number "1". Then, the server adds the number "1" to the first image block containing the predetermined type of image region, and then outputs the first image block with the number "1". For example, the server may output the first image block with the number "1" to a terminal device connected to the server. The terminal device displays the image. The terminal device here may be, for example, a device that needs to further process the fundus image block containing the predetermined type of image region. In this way, the server only needs to transmit the first image block containing the predetermined type of image region to the terminal device, thereby reducing the data transmission traffic of the server and improving the transmission speed of the server.

It can be seen from FIG. 4 that, compared with the corresponding embodiment of FIG. 2, the flow 400 of the method for processing a fundus image in the present embodiment embodies the step of adding, in response to determining that the first image block is a fundus image block containing the predetermined type of image region, a label to the first image block, and outputting the first image block with the label. According to the solution described in the present embodiment, the server only needs to output a fundus image containing a predetermined type of image region, thereby reducing the data processing amount of the server and improving the processing speed of the fundus image.

Figure 5:
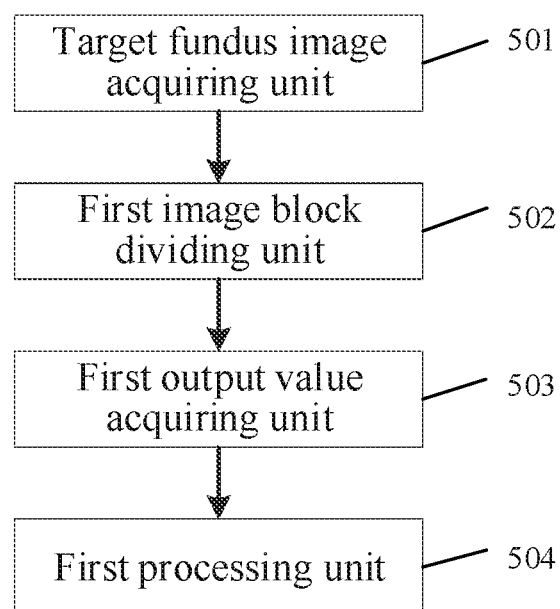
FIG. 5 is a schematic structural diagram of an apparatus for processing a fundus image according to an embodiment of the present disclosure.

Further referring to FIG. 5, as an implementation of the method shown in the above figures, some embodiments of the present disclosure provide an apparatus for processing a fundus image. The embodiment of the apparatus corresponds to the embodiment of the method shown in FIG. 2, and the apparatus may be applied to various electronic devices.

As shown in FIG. 5, the apparatus 500 for processing a fundus image according to the present embodiment includes a target fundus image acquiring unit 501, a first image block dividing unit 502, a first output value acquiring unit 503, and a first processing unit 504. The target fundus image acquiring unit 501 is configured to acquire a target fundus image; the first image block dividing unit 502 is configured to divide the target fundus image into at least two first image blocks; the first output value acquiring unit 503 is configured to input a first image block into a pre-trained deep learning model, to obtain a first output value, where the deep learning model is used to characterize a corresponding relationship between an image block and an output value; the first processing unit 504 is configured to determine, based on the first output value and a threshold, whether the first image block is a fundus image block containing a predetermined type of image region, where the threshold is determined by the following steps: acquiring a fundus image containing the predetermined type of image region, and determining the threshold based on the fundus image containing the predetermined type of image region and the deep learning model.

In the present embodiment, the specific processing of the target fundus image acquiring unit 501, the first image block dividing unit 502, the first output value acquiring unit 503, and the first processing unit 504 of the apparatus 500 for processing a fundus image and the technical effects thereof may be referred to the related description in step 201, step 202, step 203, and step 204 in the corresponding embodiment of FIG. 2, respectively. The description will not be repeated herein.

In some alternative implementations of the present embodiment, the apparatus 500 for processing a fundus image further includes an output unit (not shown). The output unit may be configured to add, in response to determining that the first image block is the fundus image block containing a predetermined type of image region, a label to the first image block, and output the first image block with the label.

In some alternative implementations of the present embodiment, the first processing unit 504 may include a comparing module, a first determining module, and a second determining module (not shown). The comparing module may be configured to determine whether the first output value is greater than the threshold. The first determining module may be configured to determine, in response to the first output value being greater than the threshold, the first image block as the fundus image block containing the predetermined type of image region. The second determining module may be configured to determine, in response to the first output value being smaller than or equal to the threshold, the first image block as a fundus image block not containing the predetermined type of image region.

In some alternative implementations of the present embodiment, the threshold may be determined by the following units: a first acquiring unit, a second output value acquiring unit, and a first threshold determining unit (not shown). The first acquiring unit may be configured to acquire fundus images containing the predetermined type of image region. The second output value acquiring unit may be configured to input the fundus images containing the predetermined type of image region into the deep learning model, to obtain second output values. The first threshold determining unit may be configured to determine the threshold from the second output values.

In some alternative implementations of the present embodiment, the threshold may be determined by the following units: a second acquiring unit, a second image block dividing unit, a third output value acquiring unit, and a second threshold determining unit (not shown). The second acquiring unit may be configured to acquire a fundus image containing the predetermined type of image region. The second image block dividing unit may be configured to divide the fundus image containing the predetermined type of image region into at least two second image blocks. The third output value acquiring unit is configured to input the at least two second image blocks into the deep learning model respectively to obtain at least two third output values. The second threshold determining unit may be configured to select a maximum value from the at least two third output values as the threshold.

In some alternative implementations of the present embodiment, the deep learning model may be obtained by training the following units: a first training sample set acquiring unit and a first training unit (not shown). The first training sample set acquiring unit may be configured to acquire a first training sample set. The first training sample includes a fundus image not containing the predetermined type of image region and a preset value matching the fundus image not containing the predetermined type of image region. The first training unit may be configured to train using fundus images not containing the predetermined type of image region in the first training sample set as inputs, and using preset values matching the input fundus images not containing the predetermined type of image region as desired outputs, to obtain the deep learning model.

In some alternative implementations of the present embodiment, the deep learning model may be obtained by training the following units: a second training sample set acquiring unit and a second training unit (not shown). The second training sample set acquiring unit may be configured to acquire a second training sample set. The second training sample includes at least two third image blocks not containing the predetermined type of image region and preset values matching the third image blocks. The at least two third image blocks not containing the predetermined type of image region are obtained by dividing the fundus image not containing the predetermined type of image region. The second training unit may be configured to train using the third image blocks in the training sample set as inputs, and using the preset values matching the third image blocks as desired outputs, to obtain the deep learning model.

According to the apparatus provided by the above embodiments of the present disclosure, a first image block dividing unit 502 divides a target fundus image acquired by a target fundus image acquiring unit 501; then, a first output value acquiring unit 503 may input a first image block into a pre-trained deep learning model to obtain a first output value; thereafter, a first processing unit may determine, based on the first output value and a threshold, whether the first image block is a fundus image block containing a predetermined type of image region. Therefore, the processing speed of a processor on the target fundus image can be improved, and the amount of calculation of the processor can be reduced.

Hereinafter, further referring to FIG. 6, a schematic structural diagram of an electronic device (e.g., the server in FIG. 1) 600 adapted to implement some embodiments of the present disclosure is shown. The server shown in FIG. 6 is merely an example, and should not limit the function and scope of use of the embodiments of the present disclosure.

Figure 6:
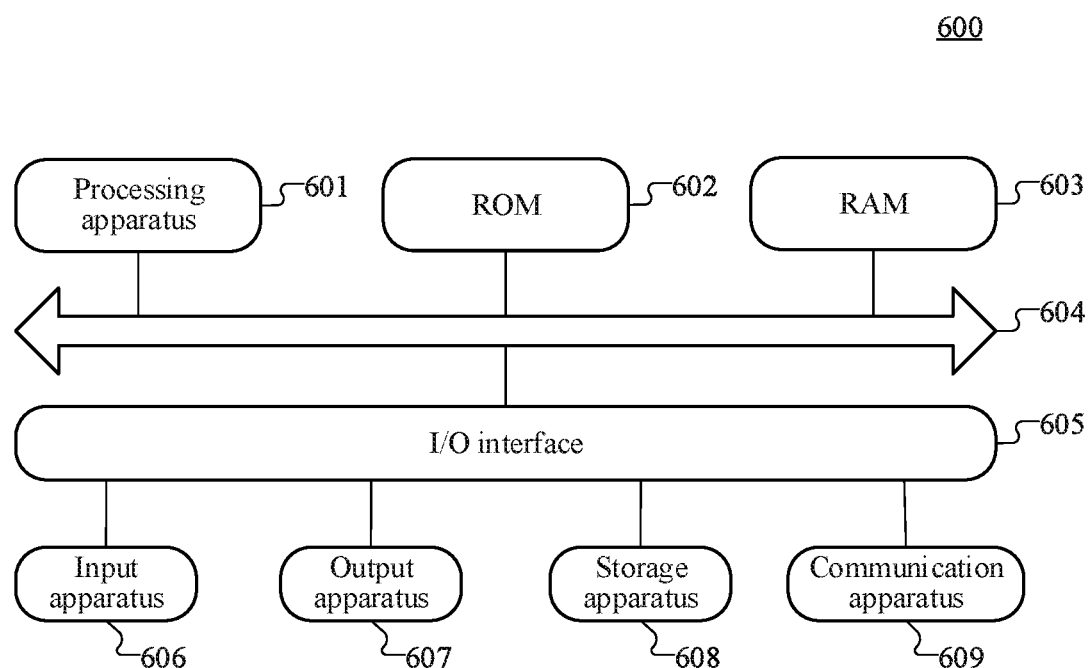
FIG. 6 is a schematic structural diagram of an electronic device adapted to implement the embodiments of the present disclosure.

As shown in FIG. 6, the electronic device 600 may include a processing apparatus (e.g., a central processing unit, a Graphics Processing Unit, etc.) 601, which may execute various appropriate operations and processes according to a program stored in a read-only memory (ROM) 602 or a program loaded into a random access memory (RAM) 603 from a storage apparatus 608. The RAM 603 also stores various programs and data required by the operations of the electronic device 600. The processing apparatus 601, the ROM 602, and the RAM 603 are connected to each other through a bus 604. An input/output (I/O) interface 605 is also connected to the bus 604.

Generally, the following apparatuses may be connected to the I/O interface 605: an input apparatus 606 including a touch screen, a touch pad, a keyboard, a mouse, a camera, a microphone, an accelerometer, a gyroscope, or the like; an output apparatus 607 including a liquid crystal display (LCD), a speaker, a vibrator, or the like; a storage apparatus 608 including a magnetic tape, a hard disk, or the like; and a communication apparatus 609. The communication apparatus 609 may allow wireless or wired communication between the electronic device 600 and other device to exchange data. Although FIG. 6 illustrates the electronic device 600 having various apparatuses, it should be understood that all the illustrated apparatuses are not required to be implemented or included. More or less apparatuses may be alternatively implemented or included. Each block shown in FIG. 6 may represent one apparatus or a plurality of apparatuses as required.

In particular, according to embodiments of the present disclosure, the process described above with reference to the flowchart may be implemented in a computer software program. For example, an embodiment of the present disclosure includes a computer program product, which includes a computer program that is hosted in a machine-readable medium. The computer program includes program codes for executing the method as illustrated in the flow chart. In such an embodiment, the computer program may be downloaded and installed from a network via the communication apparatus 609, or may be installed from the storage apparatus 608, or installed from the ROM 602. The computer program, when executed by the processing apparatus 601, implements the above functionalities as defined by the methods of the present disclosure.

It should be noted that the computer readable medium in the present disclosure may be computer readable signal medium or computer readable storage medium or any combination of the above two. An example of the computer readable storage medium may include, but not limited to: electric, magnetic, optical, electromagnetic, infrared, or semiconductor systems, apparatus, elements, or a combination any of the above. A more specific example of the computer readable storage medium may include but is not limited to: electrical connection with one or more wire, a portable computer disk, a hard disk, a random access memory (RAM), a read only memory (ROM), an erasable programmable read only memory (EPROM or flash memory), a fibre, a portable compact disk read only memory (CD-ROM), an optical memory, a magnet memory or any suitable combination of the above. In some embodiments of the present disclosure, the computer readable storage medium may be any tangible medium containing or storing programs which can be used by a command execution system, apparatus or element or incorporated thereto. In some embodiments of the present disclosure, the computer readable signal medium may include data signal in the base band or propagating as parts of a carrier, in which computer readable program codes are carried. The propagating signal may take various forms, including but not limited to: an electromagnetic signal, an optical signal or any suitable combination of the above. The signal medium that can be read by computer may be any computer readable medium except for the computer readable storage medium. The computer readable medium is capable of transmitting, propagating or transferring programs for use by, or used in combination with, a command execution system, apparatus or element. The program codes contained on the computer readable medium may be transmitted with any suitable medium including but not limited to: wireless, wired, optical cable, RF medium etc., or any suitable combination of the above.

The computer-readable medium may be included in the above electronic device, or a stand-alone computer-readable medium not assembled into the server. The computer-readable medium stores one or more programs. The one or more programs, when executed by the server, cause the server to: acquire a target fundus image, divide the target fundus image into at least two first image blocks, input a first image block into a pre-trained deep learning model to obtain a first output value, and determine, based on the first output value and a threshold, whether the first image block is a fundus image block containing a predetermined type of image region.

A computer program code for executing operations in some embodiments of the present disclosure may be compiled using one or more programming languages or combinations thereof. The programming languages include object-oriented programming languages, such as Java, Smalltalk or C++, and also include conventional procedural programming languages, such as "C" language or similar programming languages. The program code may be completely executed on a user's computer, partially executed on a user's computer, executed as a separate software package, partially executed on a user's computer and partially executed on a remote computer, or completely executed on a remote computer or server. In the circumstance involving a remote computer, the remote computer may be connected to a user's computer through any network, including local area network (LAN) or wide area network (WAN), or may be connected to an external computer (for example, connected through Internet using an Internet service provider).

The flow charts and block diagrams in the accompanying drawings illustrate architectures, functions and operations that may be implemented according to the systems, methods and computer program products of the various embodiments of the present disclosure. In this regard, each of the blocks in the flow charts or block diagrams may represent a module, a program segment, or a code portion, said module, program segment, or code portion comprising one or more executable instructions for implementing specified logic functions. It should also be noted that, in some alternative implementations, the functions denoted by the blocks may occur in a sequence different from the sequences shown in the figures. For example, any two blocks presented in succession may be executed, substantially in parallel, or they may sometimes be in a reverse sequence, depending on the function involved. It should also be noted that each block in the block diagrams and/or flow charts as well as a combination of blocks may be implemented using a dedicated hardware-based system executing specified functions or operations, or by a combination of a dedicated hardware and computer instructions.

The units or modules involved in the embodiments of the present disclosure may be implemented by means of software or hardware. The described units or modules may also be provided in a processor, for example, described as: a processor, including a target fundus image acquiring unit, a first image block dividing unit, a first output value acquiring unit, and a first processing unit. The names of these units do not in some cases constitute a limitation to such units themselves. For example, the target fundus image acquiring unit may also be described as "a unit configured to acquire a target fundus image".

The above description only provides an explanation of the preferred embodiments of the present disclosure and the technical principles used. It should be appreciated by those skilled in the art that the inventive scope of the present disclosure is not limited to the technical solutions formed by the particular combinations of the above-described technical features. The inventive scope should also cover other technical solutions formed by any combinations of the above-described technical features or equivalent features thereof without departing from the concept of the disclosure. Technical schemes formed by the above-described features being interchanged with, but not limited to, technical features with similar functions disclosed in the present disclosure are examples.

What is claimed is:

1. A method for processing a fundus image, comprising:
   acquiring a target fundus image;
   dividing the target fundus image into at least two first image blocks;
   inputting a first image block into a pre-trained deep learning model, to obtain a first output value, wherein the pre-trained deep learning model is used to characterize a corresponding relationship between an image block and an output value; and
   determining, based on the first output value and a threshold, whether the first image block is a fundus image block containing a predetermined type of image region, wherein the threshold is determined by the following steps: acquiring a fundus image containing the predetermined type of image region; dividing the fundus image containing the predetermined type of image region into at least two second image blocks; inputting the at least two second image blocks into the pre-trained deep learning model respectively to obtain at least two third output values; and selecting a maximum value from the at least two third output values as the threshold.

2. The method according to claim 1, wherein the method further comprises:
   adding, in response to determining that the first image block is the fundus image block containing the predetermined type of image region, a label to the first image block, and outputting the first image block with the label.

3. The method according to claim 1, wherein the determining, based on the first output value and a threshold, whether the first image block is a fundus image block containing a predetermined type of image region comprises:
   determining whether the first output value is greater than the threshold;
   determining, in response to the first output value being greater than the threshold, the first image block as the fundus image block containing the predetermined type of image region; and
   determining, in response to the first output value being smaller than or equal to the threshold, the first image block as a fundus image block not containing the predetermined type of image region.

4. The method according to claim 1, wherein the threshold is determined by the following steps:
   acquiring fundus images containing the predetermined type of image region;
   inputting the fundus images containing the predetermined type of image region into the pre-trained deep learning model, to obtain second output values; and
   determining the threshold from the second output values.

5. The method according to claim 1, wherein the pre-trained deep learning model is obtained by training based on a set of first training samples, wherein a first training sample in the set of first training samples only includes a fundus image not containing the predetermined type of image region and a preset value matching the fundus image not containing the predetermined type of image region.

6. The method according to claim 1, wherein the pre-trained deep learning model is obtained by training through the following steps:
   acquiring a first training sample set, wherein a first training sample comprises a fundus image not containing the predetermined type of image region and a preset value matching the fundus image not containing the predetermined type of image region; and
   training using fundus images not containing the predetermined type of image region of the first training samples in the first training sample set as inputs, and using preset values matching the input fundus images not containing the predetermined type of image region as desired outputs, to obtain the pre-trained deep learning model.

7. The method according to claim 1, wherein the pre-trained deep learning model is obtained by training through the following steps:
   acquiring a second training sample set, wherein a second training sample comprises at least two third image blocks not containing the predetermined type of image region and preset values matching the third image blocks, and the at least two third image blocks not containing the predetermined type of image region are obtained by dividing the fundus image not containing the predetermined type of image region; and
   training using the third image blocks of the second training samples in the training sample set as inputs, and using the preset values matching the third image blocks as desired outputs, to obtain the pre-trained deep learning model.

8. An apparatus for processing a fundus image, comprising:
   at least one processor; and
   a memory storing instructions, the instructions when executed by the at least one processor, cause the at least one processor to perform operations, the operations comprising:
   acquiring a target fundus image;
   dividing the target fundus image into at least two first image blocks;
   inputting a first image block into a pre-trained deep learning model, to obtain a first output value, wherein the pre-trained deep learning model is used to characterize a corresponding relationship between an image block and an output value; and
   determining, based on the first output value and a threshold, whether the first image block is a fundus image block containing a predetermined type of image region, wherein the threshold is determined by the following steps: acquiring a fundus image containing the predetermined type of image region; dividing the fundus image containing the predetermined type of image region into at least two second image blocks; inputting the at least two second image blocks into the pre-trained deep learning model respectively to obtain at least two third output values; and selecting a maximum value from the at least two third output values as the threshold.

9. The apparatus according to claim 8, wherein the operations further comprise:
adding, in response to determining that the first image block is the fundus image block containing the predetermined type of image region, a label to the first image block, and output the first image block with the label.

10. The apparatus according to claim 8, wherein the determining, based on the first output value and a threshold, whether the first image block is a fundus image block containing a predetermined type of image region comprises:
determining whether the first output value is greater than the threshold;
determining, in response to the first output value being greater than the threshold, the first image block as the fundus image block containing the predetermined type of image region; and
determining, in response to the first output value being smaller than or equal to the threshold, the first image block as a fundus image block not containing the predetermined type of image region.

11. The apparatus according to claim 8, wherein the threshold is determined by:
acquiring fundus images containing the predetermined type of image region;
inputting the fundus images containing the predetermined type of image region into the pre-trained deep learning model, to obtain second output values; and
determining the threshold from the second output values.

12. The apparatus according to claim 8, wherein the pre-trained deep learning model is obtained by training based on a set of first training samples, wherein a first training sample in the set of first training samples only includes a fundus image not containing the predetermined type of image region and a preset value matching the fundus image not containing the predetermined type of image region.

13. The apparatus according to claim 8, wherein the pre-trained deep learning model is obtained by training through:
acquiring a first training sample set, wherein a first training sample comprises a fundus image not containing the predetermined type of image region and a preset value matching the fundus image not containing the predetermined type of image region; and
training using fundus images not containing the predetermined type of image region of the first training samples in the first training sample set as inputs, and using preset values matching the input fundus images not containing the predetermined type of image region as desired outputs, to obtain the pre-trained deep learning model.

14. The apparatus according to claim 8, wherein the pre-trained deep learning model is obtained by training through:
acquiring a second training sample set, wherein a second training sample comprises at least two third image blocks not containing the predetermined type of image region and preset values matching the third image blocks, and the at least two third image blocks not containing the predetermined type of image region are obtained by dividing the fundus image not containing the predetermined type of image region; and
training using the third image blocks of the second training samples in the training sample set as inputs, and using the preset values matching the third image blocks as desired outputs, to obtain the pre-trained deep learning model.

15. A non-transitory computer-readable medium, storing a computer program thereon, wherein the computer program, when executed by a processor, causes the processor to implement operations, the operations comprise:
acquiring a target fundus image;
dividing the target fundus image into at least two first image blocks;
inputting a first image block into a pre-trained deep learning model, to obtain a first output value, wherein the pre-trained deep learning model is used to characterize a corresponding relationship between an image block and an output value; and
determining, based on the first output value and a threshold, whether the first image block is a fundus image block containing a predetermined type of image region, wherein the threshold is determined by the following steps: acquiring a fundus image containing the predetermined type of image region; dividing the fundus image containing the predetermined type of image region into at least two second image blocks; inputting the at least two second image blocks into the pre-trained deep learning model respectively to obtain at least two third output values; and selecting a maximum value from the at least two third output values as the threshold.

16. The medium according to claim 15, wherein the operations further comprise:
adding, in response to determining that the first image block is the fundus image block containing the predetermined type of image region, a label to the first image block, and outputting the first image block with the label.

17. The medium according to claim 15, wherein the determining, based on the first output value and a threshold, whether the first image block is a fundus image block containing a predetermined type of image region comprises:
determining whether the first output value is greater than the threshold;
determining, in response to the first output value being greater than the threshold, the first image block as the fundus image block containing the predetermined type of image region; and
determining, in response to the first output value being smaller than or equal to the threshold, the first image block as a fundus image block not containing the predetermined type of image region.

18. The medium according to claim 15, wherein the threshold is determined by the following steps:
acquiring fundus images containing the predetermined type of image region;
inputting the fundus images containing the predetermined type of image region into the pre-trained deep learning model, to obtain second output values; and
determining the threshold from the second output values.

19. The medium according to claim 15, wherein the pre-trained deep learning model is obtained by training based on a set of first training samples, wherein a first training sample in the set of first training samples only includes a fundus image not containing the predetermined type of image region and a preset value matching the fundus image not containing the predetermined type of image region.

20. The medium according to claim 15, wherein the pre-trained deep learning model is obtained by training through the following steps:
   acquiring a first training sample set, wherein a first training sample comprises a fundus image not containing the predetermined type of image region and a preset value matching the fundus image not containing the predetermined type of image region; and
   training using fundus images not containing the predetermined type of image region of the first training samples in the first training sample set as inputs, and using preset values matching the input fundus images not containing the predetermined type of image region as desired outputs, to obtain the pre-trained deep learning model.

\* \* \* \* \*